US012746309B2

(12) United States Patent
Reiterer et al.

(10) Patent No.: US 12,746,309 B2
(45) Date of Patent: Sep. 29, 2026

(54) TISSUE ENGINEERED VASCULAR GRAFTS

(71) Applicant: Medtronic, Inc, Minneapolis, MN (US)

(72) Inventors: Markus W. Reiterer, Plymouth, MN (US); Kimberly A. Chaffin, Woodbury, MN (US); Michael F. Wolf, Golden Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 1170 days.

(21) Appl. No.: 17/736,774

(22) Filed: May 4, 2022

(65) Prior Publication Data

US 2022/0354632 A1 Nov. 10, 2022

Related U.S. Application Data

(60) Provisional application No. 63/185,244, filed on May 6, 2021.

(51) Int. Cl.

| | |
|---|---|
| ***A61F 2/06*** | (2013.01) |
| ***A61K 31/496*** | (2006.01) |
| ***A61K 31/65*** | (2006.01) |
| ***A61L 27/38*** | (2006.01) |
| ***A61L 27/52*** | (2006.01) |
| ***C12N 5/077*** | (2010.01) |
| ***C12N 5/0775*** | (2010.01) |
| *A61F 2/00* | (2006.01) |

(52) U.S. Cl.

CPC ................ *A61L 27/38* (2013.01); *A61F 2/06* (2013.01); *A61K 31/496* (2013.01); *A61K 31/65* (2013.01); *A61L 27/52* (2013.01); *C12N 5/0661* (2013.01); *C12N 5/0663* (2013.01); *A61F 2/0063* (2013.01); *A61F 2210/0014* (2013.01); *A61F 2210/0076* (2013.01); *A61F 2240/001* (2013.01); *A61L 2400/06* (2013.01); *C12N 2513/00* (2013.01); *C12N 2533/40* (2013.01)

(58) Field of Classification Search

None

See application file for complete search history.

(56) References Cited

U.S. PATENT DOCUMENTS

| | | | |
|---|---|---|---|
| 7,744,526 | B2 | 6/2010 | McAllister |
| 8,192,348 | B2 | 6/2012 | Tranquillo |
| 8,808,362 | B2 | 8/2014 | Anwar |

(Continued)

FOREIGN PATENT DOCUMENTS

| | | | | |
|---|---|---|---|---|
| RU | 187447 U1 * | 3/2019 | .............. | A61F 2/07 |

OTHER PUBLICATIONS

Chen, et al., "Shapeable large-pore electrospun polycaprolactam cotton facilitates the rapid formation of a functional tissue engineered vascular graft," Materials and Design 191 (2020) 10863.

(Continued)

*Primary Examiner* — Thaddeus B Cox

(74) *Attorney, Agent, or Firm* — Fletcher Yoder P.C.

(57) ABSTRACT

The disclosure relates to systems and methods for tissue engineered grafts. The systems and methods can be used to make tissue engineered vascular grafts. The systems and methods use bioink deposited on a material having specified properties and matured under specified conditions to create the tissue engineered grafts having biomechanical properties tailored to a particular tissue.

10 Claims, 8 Drawing Sheets

(56) References Cited

U.S. PATENT DOCUMENTS

| | | | | |
|---|---|---|---|---|
| 9,290,742 | B2 | 3/2016 | Cooper | |
| 2002/0087176 | A1* | 7/2002 | Greenhalgh | A61F 2/064 606/155 |
| 2010/0185219 | A1 | 7/2010 | Gertzman | |
| 2013/0164339 | A1 | 6/2013 | Murphy | |
| 2014/0379072 | A1 | 12/2014 | Barbarash | |
| 2016/0288414 | A1 | 10/2016 | Ozbolat | |
| 2018/0353649 | A1 | 12/2018 | Breuer | |
| 2018/0369451 | A1* | 12/2018 | Rapoport | C09D 11/38 |
| 2019/0111088 | A1 | 4/2019 | Murphy | |
| 2020/0038211 | A1* | 2/2020 | Kölbel | A61F 2/954 |
| 2020/0139007 | A1 | 5/2020 | Kesti | |
| 2020/0197152 | A1 | 6/2020 | Murphy | |

OTHER PUBLICATIONS

Berglund, et al., "A biological hybrid model for collagen-based tissue engineered vascular constructs," Biomaterials 24 (2003) 1241-1254.
Torikai, et al, "A self-renewing, tissue-engineered vascular graft for arterial reconstruction," J Thorac Cardiovasc Surg 2008;136:37-45.
Messa, et al, "Biomechanical Parameters of Mesh Reinforcement and Analysis of a Novel Device for Incisional Hernia Prevention," Journal of Surgical Research Feb. 2021 (258) 153-161.
Wang, et al., "Degradable/non-degradable polymer composites for in-situ tissue engineering small diameter vascular prosthesis application," Bio-Medical Materials and Engineering 24 (2014) 2127-2133.
Tschoeke, et al,, "Development of a Composite Degradable/Nondegradable Tissue-engineered Vascular Graft," Artificial Organs 32(10):800-809, Wiley Periodicals, Inc.
Fernández-Colino, et al, "Textile-Reinforced Scaffolds for Vascular Tissue Engineering," Tissue-Engineered Vascular Grafts. Reference Series in Biomedical Engineering, Springer Cham. (2020) 339-363.
Bringman, et al. "Hernia repair: the search for ideal meshes," Hernia (2010) 14:81-87.
L'Heureux, et al. "Human Tissue Engineered Blood Vessel For Adult Arterial Revascularization," Nat Med. Mar. 2006 ; 12(3): 361-365.
Deeken, et al, "Mechanical properties of the abdominal wall and biomaterials utilized for hernia repair," Journal of the Mechanical Behavior of Biomedical Materials 74 (2017) 411-427.
Konig, et al, "Mechanical properties of completely autologous human tissue engineered blood vessels compared to human saphenous vein and mammary artery," Biomaterials. Mar. 2009 ; 30(8): 1542-1550.
Klinge, et al, "Modified Mesh for Hernia Repair that is Adapted to the Physiology of the Abdominal Wall," Eur J Surg 1998; 164: 951-960.
Sanbhal, et al, "Physical structure and mechanical properties of knitted hernia mesh materials: A review," Journal of Industrial Textiles 2018, vol. 48(1) 333-360.
Maurer, et al., "Prosthetic Meshes for Repair of Hernia and Pelvic Organ Prolapse: Comparison of Biomechanical Properties," Materials 2015, 8, 2794-2808.
Akentjew, et al, "Rapid fabrication of reinforced and cell-laden vascular grafts structurally inspired by human coronary arteries," Nat Commun. Jul. 15, 2019;10(1):3098.
Cobb, et al, "The Argument for Lightweight Polypropylene Mesh in Hernia Repair," Surgical Innovation, vol. 12, No. 1 Mar. 2005: pp. 63-69.
Thomas, et al, "Tissue engineered vascular grafts—Preclinical aspects," International Journal of Cardiology 167 (2013) 1091-1100.
Lim, et al, "Tissue-Engineered Blood Vessels With Endothelial Nitric Oxide Synthase Activity," J Biomed Mater Res B Appl Biomater. May 2008;85(2):537-46.

* cited by examiner

TISSUE ENGINEERED VASCULAR GRAFTS

FIELD

The disclosure relates to materials for tissue engineered grafts, methods for manufacture, and constructs made therefrom. The disclosure can be used for tissue engineered vascular grafts, A/V grafts, and compositions having regions of varying biomechanical properties. The disclosure also relates to systems, methods, and products made therefrom that use a bioink deposited or impregnated into a scaffold made from a mesh, knitted or woven material, suture materials, inter alia, to form a hybrid structure having suitable biomechanical properties for vascular grafts.

BACKGROUND

Tissue engineered vascular grafts have broad application in neurovascular, coronary artery, peripheral arterial and venous disease, as well as in dialysis including access grafts and AV shunts for hemodialysis. However, the known tissue engineered materials often lack patency or fail to have sufficient mechanical properties for successful in vivo implantation. In general, three types of grafts are known: autologous, synthetic, and tissue engineered. Each suffer from the known problems of thrombosis, intimal hyperplasia, arteriosclerosis, incomplete anastomosis, and insufficient biomechanical properties. Autologous grafts are considered the gold standard for vascular implants but often have issues related to donor site and harvesting. Donor vessels such as the saphenous vein and internal thoracic artery may have low availability, donor site morbidity, compliance mismatch, and late intimal hyperplasia, which can cause graft failure. In general, patches of tissue cannot be harvested from donors. Synthetic vascular grafts made from Dacron, Teflon, and other materials have been fabricated to meet the need for grafts but suffer from a variety of performance issues. In the case of vascular grafts, synthetic materials often result in thrombogenesis, stenosis, and occlusion. Thrombosis and vessel occlusion are particularly problematic for smaller caliber grafts. Recently, increased incidence of coronary artery disease, an older population, and obesity have created an urgent need for small-diameter vessel substitutes. These conditions commonly require bypass surgery to replace diseased and damaged arteries having an inner diameter less than 6 mm. Vascular grafts are susceptible to infection and lack of growth potential. Although synthetic polymers such as polytetrafluoroethylene ("PTFE") and polyurethane have been used due to their antithrombogenic and mechanical properties, thrombus formation and infection still pose a problem.

To overcome the thrombogenic limitations of synthetic materials, tissue engineered vascular grafts containing autologous or allogeneic cells have been developed. However, these materials generally exhibit poor biomechanical and strength properties. The first tissue-engineered blood vessel construct was produced in the mid-1980s using bovine endothelial cells, fibroblasts, and smooth muscle cells. The tissue engineered materials used autologous cell seeding to improve anti-thrombogenicity and material performance. The cells were co-cultured in a collagen matrix and then shaped into tubes using a molding technique. Although tissue architectures analogous to natural blood vessels were fabricated, the known constructs required the support of a Dacron mesh and possessed poor mechanical properties. Other known approaches require the use of various materials, manufacturing methods, cell sources, and culture protocols based on a scaffold using synthetic or natural materials or a decellularized natural matrix and self-assembly processes. Electro-spinning or electro-static preparation of materials have also been used to form a scaffold from various polymers. Sometimes a scaffold or stabilizing material is used to retain the autologous cell seeding during a growth period whether in a bioreactor or in vivo. Hydrogels or collagens have been used as a substrate for autologous cells such as smooth muscle cells.

However, the known tissue engineered materials whether formed via molding, electrospinning (or electro-static), seeding, or other techniques using various stabilizing constructs such as scaffolds, continue to suffer biomechanical failure. The known materials frequently result in clinical complications such as infection, chronic inflammation, or growth failure. Although techniques have been developed to address these limitations, such as endothelializing surfaces of a vessel to reduce thrombogenicity, limitations in material properties remain. For example, the known tissue engineered materials exhibit limitations in mechanical integrity such as hyperplasia (bulging) and insufficient suture retention. The known tissue engineered vessels also often fail to withstand normal physiological pressure such as specified burst pressure or tensile strength and exhibit suboptimal compliance and creep properties. In addition to insufficient compliance, absorption time, and suture retention strength properties, the known tissue engineered materials cannot provide variable or different regions or areas of mechanical strength. Mismatch of mechanical properties of the implant material, as compared to surrounding native tissue can result in clinical complications. The known arteriovenous (AV) grafts do not have sections of different material properties such that an arterial side of the AV graft is matched to the mechanical properties of arterial tissue or a venous side of the AV graft is matched to vein tissue. As a result, the known AV grafts and access ports have low patency rates and fail at the AV graft/local tissue interface resulting in increased hospitalizations, cost, and suboptimal outcomes.

Hence, there is a need for materials, methods for manufacture, and products made therefrom that can be used to generate tissue engineered vascular grafts that exhibit adequate strength, longevity, and safety while having the desired physical properties for successful implantation in a patient. The need extends to materials, methods for manufacture, and products made therefrom for use in neurovascular, coronary artery, peripheral arterial and venous disease. The need extends to materials, methods for manufacture, and products made therefrom for use in dialysis including access grafts and AV shunts for hemodialysis. The need includes materials, methods for manufacture, and products made therefrom that can be bioresorbable, biodegradable, or biostable. The need extends to materials, methods for manufacture, and products made therefrom to make a tissue engineered vascular graft that has sufficient mechanical properties for surgical in vivo implantation and retention. The need includes a tissue engineered material having regions of different mechanical characteristics as might be desirable in an A/V shunt. The need extends to materials, methods for manufacture, and products made therefrom having desirable erosion kinetics that occur after a maturation phase. The need extends to materials, methods for manufacture, and products made therefrom into a vessel that can be securely sutured in a host location. The need extends to materials, methods for manufacture, and products made therefrom that has desirable material compliance and creep properties. The need extends to materials, methods for manufacture, and products made therefrom that can withstand a specific burst pressure. The need extends to materials, methods for manufacture, and products made therefrom that has sufficient mechanical integrity. The need extends to materials, methods for manufacture, and products made therefrom having desired erosion kinetics to match a desired absorption time. The need extends to materials, methods for manufacture, and products made therefrom having mechanical integrity. The need extends to materials, methods for manufacture, and products made therefrom that can integrate properly at an implantation site. The need extends to materials, methods for manufacture, and products made therefrom that can withstand a normal physiological arterial pressure and/or withstand a specified burst pressure. The need extends to materials, methods for manufacture, and products made therefrom suitable for a desired pressure amplitude. The need also includes materials, methods for manufacture, and products made therefrom suited for repeated cycling between diastolic and systolic blood pressure. The need extends to materials, methods for manufacture, and products made therefrom having variable or different regions or areas of mechanical strength. The need extends to materials, methods for manufacture, and products made therefrom that can interface and integrate with host tissue at the site of implantation and control infection. The need extends to anchoring components such as stabilization hooks that can integrate a tissue engineered construct with surrounding tissue. The need includes use of additive techniques such as 3D printing alone or combined with a rotating lathe or mandrel on which materials can be deposited thereon.

SUMMARY OF THE INVENTION

The problem to be solved is a tissue engineered material for medical use having suitable mechanical properties for in vivo implantation. The solution provides for a method of generating a vascular graft using additive techniques with a rotating mandrel.

The first aspect relates to a method for forming a tissue engineered vascular graft. In any embodiment, the method can include the step of positioning a braid tube concentrically over a bioink tube to form the vascular graft, wherein the bioink tube is previously deposited as a bioink layer on a rotating mandrel.

In any embodiment, the step of positioning the braid tube can be performed by pulling the braid tube over the bioink tube on the mandrel. The braid tube can possess elasticity about the braid tube's radius such that braid tube can be pulled over the bioink tube without damaging the bioink.

In any embodiment, the step of positioning the braid tube can be performed by interlacing filaments concentrically over the bioink tube on the mandrel.

In any embodiment, the braid tube can be expandable to a first diameter and contractible to a second diameter under axial loading.

In any embodiment, wherein the braid tube can be any one of a woven, knitted, braided, or non-woven textile.

In any embodiment, wherein the braid tube can be made of nitinol.

In any embodiment, the bioink can be deposited on the rotating mandrel using 3D printing, dip casting, or slot casting.

In any embodiment, the braid tube can be positioned concentrically over a stabilization tube prior to pulling over the concentric bioink tube, and further comprising the step of pulling out the stabilization tube once positioned on the bioink tube and leaving the braid tube behind over the concentric bioink tube to form the vascular graft.

In any embodiment, the stabilization tube can be any one of polytetrafluoroethylene, poloxamer, and combinations thereof.

In any embodiment, a sacrificial layer can be deposited on the rotating mandrel prior to the bioink layer being deposited on the rotating mandrel.

In any embodiment, the sacrificial layer can be a poloxamer layer.

In any embodiment, the method can also include the step of removing the sacrificial layer.

In any embodiment, the cell growth medium can include water, nutrients, and cell signaling chemicals.

In any embodiment, an endothelial cell layer can be deposited on the sacrificial layer on the rotating mandrel.

In any embodiment, one or more smooth muscle cell layer, fibroblast layer, cord-blood derived cell layer, or combinations thereof can be deposited on the sacrificial layer.

In any embodiment, the bioink can include a hydrogel and cells.

In any embodiment, the hydrogel can be synthetic, hybrid or natural.

In any embodiment, the hydrogel can include substances for cross-linking by physical or chemical means.

In any embodiment, the method can include additional steps for removing the vascular graft from the mandrel and maturing the vascular graft in a bioreactor under defined conditions of oxygen partial pressure and a growth medium to form the vascular graft.

In any embodiment, a pulsatile, axial loading force can be applied to the vascular graft.

In any embodiment, an interior diameter of the bioink tube can be flushed with endothelial cells in the bioreactor.

In any embodiment, one or more nutrition factors and signaling chemicals can be added to the growth medium in the bioreactor.

In any embodiment, the braid tube can be biodegradable, bioabsorbable, or bioinert.

The features disclosed as being part of the first aspect can be in the first aspect, either alone or in combination, or follow any arrangement or permutation of any one or more of the described elements. Similarly, any features disclosed as being part of the first aspect can be in a second, third, or fourth aspect described below, either alone or in combination, or follow any arrangement or permutation of any one or more of the described elements.

The second aspect relates to a method for forming a tissue engineered vascular graft having the steps of positioning a braid tube concentrically over a mandrel and depositing a bioink layer onto the braid tube on a rotating mandrel to form the vascular graft.

In any embodiment, the step of positioning the braid tube can also include pulling the braid tube over the mandrel.

In any embodiment, the step of positioning the braid tube can also include interlacing filaments concentrically over the mandrel.

In any embodiment, the braid tube can be expandable to a first diameter and contractible to a second diameter under axial loading.

In any embodiment, the braid tube can be any one of a woven, knitted, braided, or non-woven textile.

In any embodiment, the bioink can be deposited on the braid tube using 3D printing, dip casting, or slot casting.

In any embodiment, the braid tube can be positioned concentrically over a stabilization tube prior to depositing the bioink layer.

In any embodiment, the stabilization tube can be polytetrafluoroethylene, poloxamer, and combinations thereof.

In any embodiment, one or more smooth muscle cell layer, fibroblast layer, cord-blood derived cell layer, or combinations thereof are deposited on the bioink layer.

In any embodiment, the bioink can include a hydrogel and cells.

In any embodiment, the hydrogel is synthetic, hybrid or natural.

In any embodiment, the steps of removing the vascular graft from the mandrel and maturing the vascular graft in a bioreactor under defined conditions of oxygen partial pressure and a growth medium to form the vascular graft can be included.

In any embodiment, a surface of the bioink tube can be flushed with endothelial cells in the bioreactor.

In any embodiment, one or more nutrition factors and signaling chemicals can be added to the growth medium in the bioreactor.

In any embodiment, the braid tube can be biodegradable, bioabsorbable, or bioinert.

The features disclosed as being part of the second aspect can be in the second aspect, either alone or in combination, or follow any arrangement or permutation of any one or more of the described elements. Similarly, any features disclosed as being part of the second aspect can be in the first, third, or fourth aspect, either alone or in combination, or follow any arrangement or permutation of any one or more of the described elements.

The third aspect is drawn to a method. In any embodiment, the method can include the steps of forming a tissue engineered vascular graft including the steps of pulling a braid tube off a mandrel, the braid tube positioned concentrically to the mandrel, wherein the braid tube has a bioink layer previously deposited over the braid tube; and inverting the braid tube to from the vascular graft, wherein an inner surface of the vascular graft is the bioink tube and an outer surface of the vascular graft is the braid tube.

In any embodiment, the bioink can be deposited on the rotating mandrel using 3D printing, dip casting, or slot casting.

In any embodiment, the step of inverting the braid tube can be performed by pulling the braid tube off the mandrel inside out.

In any embodiment, the step of positioning a support mesh on the bioink layer prior to the step of pulling the braid tube off the mandrel to form the inverted hybrid construct can be included.

In any embodiment, the mesh can be constructed from a fast-degrading polymer.

In any embodiment, wherein the braid tube is expandable to a first diameter and contractible to a second diameter under axial loading.

In any embodiment, the braid tube can be any one of a woven, knitted, braided, or non-woven textile.

In any embodiment, the method can also include the steps of maturing the vascular graft in a bioreactor under defined conditions of oxygen partial pressure and a growth medium to form the vascular graft.

In any embodiment, a pulsatile, axial loading force can be applied to the vascular graft.

In any embodiment, one or more nutrition factors and signaling chemicals can be added to the growth medium in the bioreactor.

In any embodiment, endothelial cells can be added to the growth medium in the bioreactor.

In any embodiment, the braid tube can be biodegradable, bioabsorbable, or bioinert.

In any embodiment, the bioink layer can be seeded with endothelial cell.

In any embodiment, one or more smooth muscle cell layer, fibroblast layer, cord-blood derived cell layer, or combinations thereof can be deposited on the bioink layer.

In any embodiment, the bioink can include a hydrogel and cells.

In any embodiment, the hydrogel can be synthetic, hybrid or natural.

In any embodiment, the hydrogel can also include substances for cross-linking by physical or chemical means.

In any embodiment, the bioink layer previously deposited on the mandrel can be formed by rotating the mandrel while depositing the bioink layer to form the bioink tube.

In any embodiment, the bioink layer can include hydrogel and cells.

The features disclosed as being part of the third aspect can be in the third aspect, either alone or in combination, or follow any arrangement or permutation of any one or more of the described elements. Similarly, any features disclosed as being part of the third aspect can be in the sixth, seventh, or eighth aspect, either alone or in combination, or follow any arrangement or permutation of any one or more of the described elements.

The fourth aspect relates to a tissue engineered vascular graft made from any one of the first, second, or third aspects wherein the tissue engineered vascular graft has an inner diameter of around 2 to 12 mm and has a burst pressure strength of around 2,900 to around 4,000 mmHg.

The features disclosed as being part of the fourth aspect can be in the fourth aspect, either alone or in combination, or follow any arrangement or permutation of any one or more of the described elements. Similarly, any features disclosed as being part of the fourth aspect can be in the first, second, or third aspect, either alone or in combination, or follow any arrangement or permutation of any one or more of the described elements.

The fifth aspect relates to a tissue engineered arteriovenous graft made from any one of the first, second, or third aspects wherein the vascular graft has an inner diameter of around 1.5 mm to 2 mm and has a burst pressure strength of around 1,500 to around 6,000 mmHg.

The features disclosed as being part of the fifth aspect can be in the fifth aspect, either alone or in combination, or follow any arrangement or permutation of any one or more of the described elements. Similarly, any features disclosed as being part of the fifth aspect can be in the first, second, or third aspect, either alone or in combination, or follow any arrangement or permutation of any one or more of the described elements.

The sixth aspect is drawn to a vascular graft made from any one of the first, second, or third aspects wherein the vascular graft has a burst pressure strength of around 1,500 to around 2,000 mmHg.

The features disclosed as being part of the sixth aspect can be in the sixth aspect, either alone or in combination, or follow any arrangement or permutation of any one or more of the described elements. Similarly, any features disclosed as being part of the sixth aspect can be in the first, second, or third aspect, either alone or in combination, or follow any arrangement or permutation of any one or more of the described elements.

The seventh aspect is drawn to a vascular graft made from any one of the first, second, or third aspects wherein the tissue engineered vascular graft has a burst pressure strength of around 2,000 to around 4,500 mmHg.

The features disclosed as being part of the seventh aspect can be in the seventh aspect, either alone or in combination, or follow any arrangement or permutation of any one or more of the described elements. Similarly, any features disclosed as being part of the seventh aspect can be in the first, second, or third aspect, either alone or in combination, or follow any arrangement or permutation of any one or more of the described elements.

DETAILED DESCRIPTION

Figure 1A:
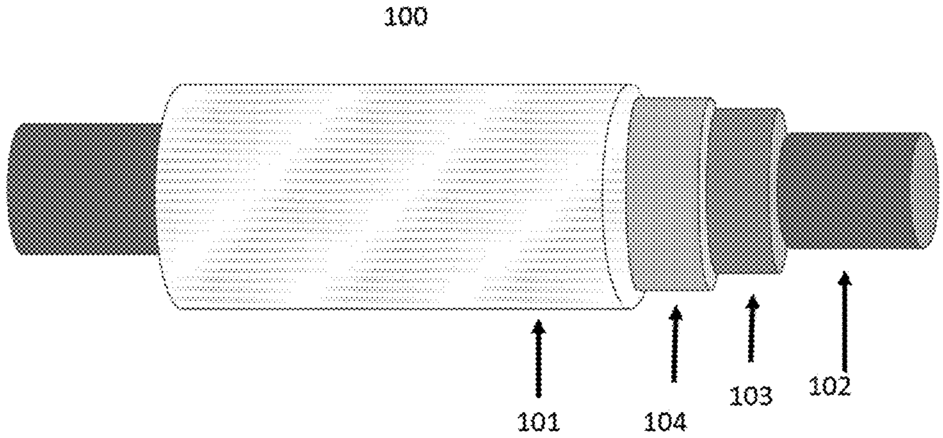
FIGS. 1A-E illustrate a process of generating a tissue engineered vascular graft using a sacrificial layer.

Unless defined otherwise, all technical and scientific terms used have the same meaning as commonly understood by one of ordinary skill in the art.

The articles "a" and "an" are used to refer to one to over one (i.e., to at least one) of the grammatical object of the article. For example, "an element" means one element or over one element.

The term "arterial end" refers to a portion of an arteriovenous graft designed to connect to an artery.

The term "arteriovenous graft" refers to a graft that connects an artery and a vein.

"Axial loading" refers to a force applied to a structure along an axis of the structure. The force can be applied in any direction relative to the axis of the structure.

The term "braiding" or "braided" refers to a process or resulting construct made by interlacing any number of threads or filaments in such a way that the threads or filaments cross one another. Braiding or braided is defined under the broadest definition to be any means, method, or procedure known to those of skill in the art to form a regular geometry of the filaments by braiding, weaving, knitting, or similar process. The braided filaments can be made of threads, cords, lines, string, or any other filaments that are interlaced, knitted, woven, or weaved together in any form or configuration using any known suitable material for the intended use.

The term "bioabsorbable" refers to a material that can be degraded and adsorbed into tissue.

The term "biodegradable" refers to a material that can be transformed or altered by an organism.

The term "bioinert" refers to a material that does not interact chemically with surrounding tissues of an organism.

The term "bioink" can be any substance containing one or more type of cells, e.g., autologous cells, of any kind and a carrier material of any type. Typically, the "bioink" will be formulated for deposition using an additive technique such as 3D printing or similar, however, such requirement is not always necessary. The broadest scope of "bioink" is intended without any limitation, or actual use in a 3D printing technique.

A "bioink tube" can be a tubular structure formed of a bioink of any type, state, or configuration. For example, bioink deposited on a mandrel will form a tube of bioink, i.e., a "bioink tube." The broadest reasonable interpretation is intended.

A "bioink layer" can be a coating of bioink on top of or around a material or component. For example, bioink material deposited on a mandrel will form a layer of bioink, i.e., a "bioink layer." The broadest reasonable interpretation is intended. Notably, multiple layers of "bioink" can be deposited on a substrate to form a "bioink layer" and in turn the "bioink layer" formed into a "bioink tube," as described herein.

A "bioreactor" is a structure in which a biological process is carried out.

A "braid tube" can be a three-dimensional tubular structure, generally cylindrical in shape with openings on each end with a hollow center of the structure connecting each end. The braid tube can be made of filaments that are interlaced, knitted, woven, or weaved together in any form or configuration by any known means, method, or procedure known to those of skill in the art to form a regular geometry of the filaments by braiding, weaving, knitting, or similar process. The braid tube can be pre-manufactured or formed by a spool over or on another material. The braid tube can be made from any suitable material, and in certain non-limiting embodiments, can be biodegradable, bioabsorbable, or bioinert.

The term "burst pressure strength" refers to a pressure that exceeds the tensile strength of a tube, causing rupturing of a material. Typically, the burst pressure strength is used for describing the strength of a tube, but any material such as a sheet, container, vessel, envelope, or enclosure is contemplated.

The term "cells" refers to the basic membrane bound unit of an organism.

A "cell layer" is a layer of any thickness comprising one or more cells, as described herein.

The term "comprising" includes, but is not limited to, whatever follows the word "comprising." Use of the term indicates the listed elements are required or mandatory but that other elements are optional and may be present.

The term "concentric" or "concentrically" refers to circles, tubes, cylinders, or shape of any kind sharing a common central axis.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "contractible" refers to a capability of decreasing in size, volume, length, circumference, or any physical measurement of an object.

The term "cord-blood derived cell" refers to cells either taken from or derived from cells taken from the umbilical cord and/or placenta.

A "cord-blood derived cell layer" is a layer of any thickness comprising one or more fibroblast cells, as described herein.

The phrase "cross-linking" with respect to "hydrogels" as defined herein, refers to any process whereby the mechanical integrity and degradation resistance of a hydrogel can be changed by chemical, biochemical, or physical means. For example, the hydrogels can respond to physical inputs such as temperature, pressure, and light. The hydrogels can also respond to chemical inputs such as pH, glucose, oxidants, and biological agents such as enzymes or amino acids.

The term "defined conditions" refer to specific values for parameters used in a process, or a range of values for parameters used in a process.

The term "deposit" or "depositing" refers to the process of placing a material onto or within a second material by any means, method, or process. "Depositing" can encompass a variety of methods of placing the material onto or within the second material, including but not limited to, 3D printing, dip casting, or slot casting.

The term "diameter," as used herein, refers to a length between two opposite sides of a component or structure, typically of a generally circular shape.

The term "dissolving" or to "dissolve" refers to a process by which a material is incorporated into a liquid solvent.

The term "dip casting" refers to any process whereby one component is dipped into a liquified material and then solidified by any means. For example, a male permanent mold can be dipped into a liquified material and then removed from liquified material to solidify on the male mold before the solidified shell is removed.

"Endothelial cells" are cells that line human blood vessels.

The term "endothelial cell layer" refers to a layer of cells of a type found lining the interior of blood vessels, lymph vessels, and the heart.

The term "expandable" refers to a capability of increasing in size, volume, or circumference.

A "fast-degrading polymer" is a polymeric material that will degrade under expected conditions in shorter time relative to another time. In one non-limiting embodiment, a "fast-degrading" polymer implanted in an organism can degrade within 3 months. In one non-limiting embodiment, a "fast-degrading" polymer implanted in an organism can degrade within 2 months. In one non-limiting embodiment, a "fast-degrading" polymer implanted in an organism can degrade within 1 month. A person of ordinary skill will understand the relative quickness described as being "fast-degrading" will depend on the material, application, and location in which the material degrades. Notably, one application of a fast degrading material can be during manufacturing. For example, during maturation in a bioreactor, a fast-degrading polymer can degrade in a range of 3 to 14 days. In vivo, a fast degrading material can degrade in a range of 1 to 3 months. One of ordinary skill will understand that fast degrading can depend and be selected to the desired application, as described herein.

A "fibroblast" or "fibroblast cell" is a biological cell that synthesizes an extracellular matrix and collagen by producing a structural framework (stroma) for tissues.

A "fibroblast layer" is a layer of any thickness comprising one or more fibroblast cells, as described herein.

The term "forming," or to "form" refers to combining together parts or components to generate a material or object of any type.

"Growth medium" refers to a composition containing water, nutrients, and cell signaling chemicals necessary to cause immature cells to mature and proliferate.

The term "hybrid hydrogel" refers to a hydrogel, as defined herein, containing a network of both synthetic and natural polymers in any combination.

The term "hydrogel" refers to a hydrogel is a three-dimensional (3D) network of hydrophilic polymers that can swell in water and hold water while maintaining the structure due to chemical or physical cross-linking of individual polymer chains. One or more components of any suitable type can be added to the hydrogel.

The term "inner diameter," as used herein, refers to a length between interior faces of two opposite sides of a component or structure, typically of a generally circular shape.

The term "interlacing" refers to a process of braiding multiple filaments using a spool to form a braid. In one non-limiting embodiment, a braided tube can be formed by interlacing filaments from a spool onto a rotating mandrel.

The terms "inverting" or to "invert" refer to a process of switching the relative locations of two components or materials. For example, an inverted tube refers to an interior now being an exterior, and vice versa.

The term "inverted construct" refers to a structure having relative an ordering of material layers that is opposite to that of the structure prior to inversion.

The term "knitting" refers to a process of interlacing thread or filaments in a series of connected loops. The term "knitted" describes a component fabricated by the process of "knitting."

The term "leaving" or to "leave" refers to keeping a component or material in a position while moving or removing one or more components from a structure or system.

A "mandrel" is a round shaft, cylindrical axle, or rod around which another material can be placed or constructed.

The terms "maturing" or to "mature" when referring to cells refers to the process of undergoing developmental changes for a cell to attain another functional state.

The term "mesh" refers to any knit, woven, or knotted fabric of any type. In general, the mesh can be comprised of porous material made of a network of wire or thread of any type.

The term "natural hydrogel" refers to a hydrogel, as defined herein, containing a network of naturally derived polymers.

"Nitinol" is a metal alloy of nickel and titanium.

"Non-woven textiles" are fabrics created by methods other than weaving, knitting, or braiding. For example, nonwoven textile can be made from staple fibers and long fibers bonded together by chemical, mechanical, heat or solvent treatment.

The term "nutrients" or "nutrient factors" refer to any chemicals or biochemicals used by living cells.

The term "oxygen partial pressure" refers to the percentage of a total pressure of gas that is attributable to oxygen.

"Polytetrafluoroethylene" or "PTFE" refers to a synthetic fluoropolymer of tetrafluoroethylene.

The terms "position," "positioned," "positioning," and the like, refer to placing a material or component in a specified location relative to other materials or components.

The term "previously" refers to an action taken or performed earlier in time than a second action.

The term "prior" refers to an action taken or step performed earlier in time than a second action or step.

The term "pulling" generally refers to exerting force so as to cause movement of any object. For example, the phrase "pulling off" refers to a process of removing a component or material from a larger structure by applying force to move the component out of the structure. Similarly, the phrase "pulling over" refers to a process of exerting force to cause movement of a first component or layer of material to move over a second component or layer of material.

The term "pulsatile" refers to a force applied to a structure with periodic variations.

The terms "removing" or to "remove" refer to a process of taking a component or portion of a component out of a larger construction or system.

The terms "rotating" or to "rotate" refer to a component turning about an axis.

The term "sacrificial layer" refers to a material that is part of a larger system or structure that can be dissolved or otherwise removed before or during any step in a process. In one non-limiting examples, a sacrificial layer can be deposited during manufacturing or process step to provide a support structure for another layer, and then removed in a subsequent step.

The terms "seeding" or to "seed" refer to a process of placing cells to be grown onto a material.

"Signaling chemicals," or cytokines, are molecules that cause cells to control a process.

The term "slot casting" refers to process of depositing a thin liquid film onto a substrate. The film thickness of the liquid film can be controlled by the flow rate and speed of the deposition means.

The term "smooth muscle cells" refers to any non-striated muscle cells generally found lining the inside of hollow organs.

The term "smooth muscle cell layer" refers to a layer of non-striated muscle cells.

The term "synthetic hydrogel" refers to a hydrogel, as defined herein, containing a network of synthetic polymers. Any combination of one or more synthetic polymers is contemplated.

A "stabilization tube" can be a three-dimensional tubular structure. The three-dimensional structure is generally cylindrical with openings on each end with a hollow center of the structure connecting each end. One non-limiting purpose of the "stabilization tube" is to provide a support for another material that can be deposited on an exterior of the stabilizing tube, thereby providing a support structure in the form of a tube. The stabilization tube can be made of a rigid or a flexible material. In any embodiment, the stabilization tube can be made of any suitable non-stick material known to one of ordinary skill in the art. In any embodiment, the tube can be made of Polytetrafluoroethylene (PTFE) or other simile synthetic fluoropolymers of tetrafluoroethylene.

The term "three-dimensional printing" or "3D printing" is a type of additive manufacturing using a CAD model or a digital 3D model. The process can include material being deposited, joined or solidified under computer control to create a three-dimensional object. In one non-limiting example, a material, such as a "bioink" as described herein, can be added layer by layer on a rotating mandrel to form a tubular structure.

The phrase "tissue-engineered," with respect to a graft, refers to any biomaterial, natural material, or combinations thereof, combined or formed into any type of tissue.

A "tubular braid" refers to a three-dimensional braided material having a hollow cylindrical shape. The braid can be made of any number of interlaced filaments or strands.

A "vascular graft" is a tubular structure intended to replace a blood vessel or vasculature of any type.

The term "venous end" refers to a portion of an arteriovenous graft designed to connect to a vein.

The term "woven" can refer to any material or component fabricated by interlacement of warp and weft yarn. In general, warp and weft are the two basic components used in weaving wherein lengthwise or longitudinal warp yarns are held stationary in tension on a frame or loom while the transverse weft is drawn through and inserted over-and-under the warp.

Tissue Engineered Vascular Graft

Figure 1B:
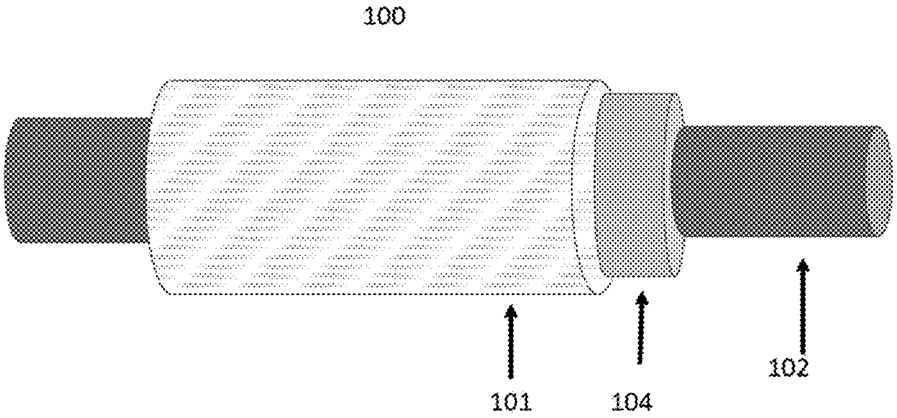
Figure 1C:
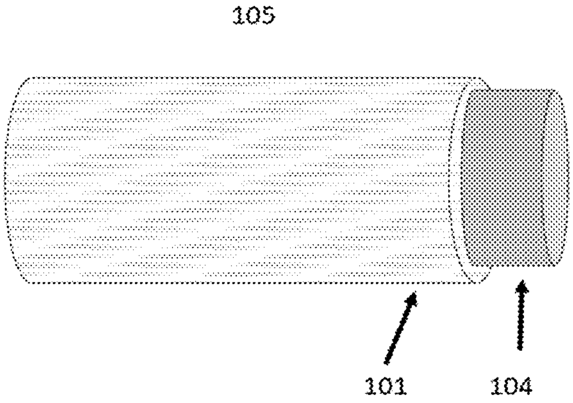

FIGS. 1A-F illustrate systems and methods for making tissue engineered vascular graft. The vascular graft 105 shown in FIG. 1C is made from a braid tube 101 printed or otherwise deposited on a bioink tube 104 that is concentric to a sacrificial layer 103 as shown in FIG. 1A. The sacrificial layer 103 is first printed or deposited on a cylindrical mandrel 102 in the system 100 of FIG. 1A as shown. The sacrificial layer 103 can be printed or deposited onto mandrel 102 and serve as a release layer, and can be made from a poloxamer, e.g., Pluronic® or similar material. The mandrel 102 of system 100 can be rotated as the sacrificial layer 103 is printed or deposited on the circumference of the mandrel 102 using an additive-lathe 3D printer rotating in a direction to replace a y-direction of a Cartesian system. Alternatively, dip casting, slot casting, and other suitable methods can also be used to deposit material on the mandrel 102. Once the sacrificial layer 103 has been formed, the bioink tube 104 can be formed next by bio-printing, printing, or otherwise, additively layering bioink on top of sacrificial layer 103 similar to the process used to form the sacrificial layer 103. Alternatively, different methods can be used or in combination. For example, the first step, can rely on dip-casting the sacrificial layer 103, but the 3D lathe printing used for the bioink tube 104.

In any embodiment, the bioink used in bioink tube 104 can contain a carrier material and autologous cells such as smooth muscle cells. Any suitable carrier material known in the art can be used for the bioink tube 104. In any embodiment, the carrier can be a hydrogel. The hydrogel can be synthetic, hybrid or natural. In any embodiment, the hydrogel can include substances for cross-linking by physical or chemical means. In certain embodiments, the bioink tube 104 can be a hydrogel loaded with smooth muscle cells and fibroblasts. Other suitable autologous cells for reducing thrombogenesis or suitable for use in a vascular graft can be used, as described further herein.

Once the bioink tube 104 is formed as a concentric layer over the sacrificial layer 103, a braid tube 101 can be positioned concentrically over the bioink tube 104. The braid tube 101 can function as a scaffold with tailorable, mechanical properties, as described herein, to provide suitable mechanical properties for successful implantation and matching of biomechanical properties to adjacent tissue in vivo. In particular, the autologous cells in the bioink tube 104 can impregnate the scaffold structure provided by the braid tube 101 to provide anti-thrombogenic properties while the braid tube 101 provides mechanical stability to the vascular graft 105. In one non-limiting embodiment, the braid tube 101 is pre-fabricated wherein the braid tube 101 tube is formed prior to being positioned on the mandrel 101. In certain embodiments, the braid tube 101 tube can be coated with a negatively charged synthetic material to avoid red blood cells and platelet aggregation.

The braid tube 104 can be made of any non-woven textile, yarn, suture material, woven textile, knitted textile, or braided textile of any design or suitable material. In other non-limiting embodiments, the braid tube 101 can be made from any one or combination of a biodegradable, bioabsorbable, or bioinert material, as described herein. Alternatively, the braid tube 101 can be formed directly onto the surface of the bioink tube 104 using a spool that interlaces one or more filaments concentrically directly over the bioink tube 104 as the mandrel 102 rotates. In certain embodiments, the braid tube 101 can be constructed like a Chinese finger trap wherein the diameter of the braid tube 101 changes as the length of the braid tube 101 changes. For example, the diameter of the braid tube 101 can increase when the length of the braid tube 101 is shortened. Conversely, the diameter of the braid tube 101 can decrease as the length of the braid tube 101 is lengthened.

During fabrication, the braid tube 101 can be pulled over or slipped onto the bioink tube 104 over an unobstructed end of the mandrel 102. For example, the mandrel 102 can be removed off a rotating lathe in the system 100 so that an end of the mandrel 102 is unconnected. Next, the sacrificial layer 103 can be dissolved to result in the system 100 having the braid tube 101 deposited on the bioink tube 104 on the mandrel 102 as shown in FIG. 1B. A radial space remaining by the dissolved sacrificial layer 103 in the system 100 provides sufficient radial clearance such that the bioink tube 104 concentric to the braid tube 101 can be easily pulled off the mandrel 102. Alternatively, the sacrificial layer 103 can be a release layers made of a slippery material to assist in removing the material off the mandrel 102.

In FIG. 1C, the resulting vascular graft 105 can be a hollow cylindrical structure with the bioink tube 104 now serving as an inner surface of the vascular graft 105 and the braid tube 101 being an outer surface of the vascular graft 105. The vascular graft 105 can now be placed in bioreactor (not shown) to mature cells and to create a de novo extra cellular matrix. In certain embodiments, the vascular graft 105 can be seeded at this time with endothelial cells or other suitable cells on the inner lumen or on the bioink tube 101. Notably, seeding can occur at any desired point during the production process. Once prepared, the vascular graft 105 can be matured under pulsatile hydraulic and axial loading until desired properties are obtained. Without being limited to any single theory, in embodiments where the braid tube 101 is constructed in the form of a Chinese finger trap, pulsatile loading can assist in impregnation of the seeded cells into the vascular graft 105 to result in desired biomechanical properties.

In FIG. 1A, the braid tube 101 is concentric to the bioink tube 104, the sacrificial layer 103, and the mandrel 102. Although illustrated as covering only a portion of the bioink tube 104, the braid tube 101 can cover the entire length of the bioink tube 104. Similarly, the bioink tube 104 can cover the entire length of the sacrificial layer 103. As described herein, the sacrificial layer 103 can be made of a material that can be dissolved or easily removed off the mandrel 102. In certain embodiments, a poloxamer, such as Synperonics, Pluronic®, and Kolliphor can be used as the sacrificial layer 103. Poloxamers are a class of materials that have a paste-like structure at room temperature but are liquid at lower temperatures. The poloxamers can be dissolved without damaging the bioink tube 104. In certain embodiments, the sacrificial layer 103 can be removed by lowering a temperature. One of skill in the art will understand that other dissolvable materials can be used as the sacrificial layer 103 that avoid damaging the bioink tube 104. In certain embodiments, a low friction material that can be pulled off the mandrel 102 can be used as the sacrificial layer 103. For example, a tube made of polytetrafluoroethylene ("PTFE") can be used to form the sacrificial layer 103. Once the braid tube 101 is positioned over the bioink tube 104, the sacrificial layer 103 made from PTFE can be easily pulled off the mandrel 102 to form the vascular graft 105.

Figure 1D:
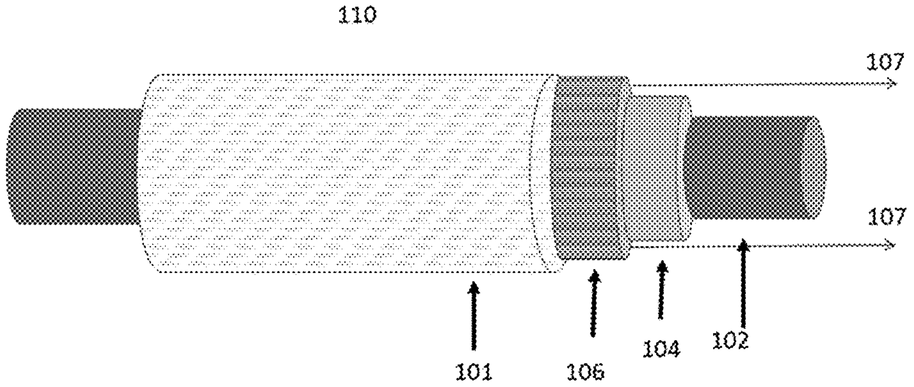

In FIG. 1D, a stabilization tube 106 can be used to assist in properly positioning the braid tube 101 concentrically over the bioink tube 104 in a system 110. In one non-limiting embodiment, the braid tube 101 is first positioned on top of the stabilization tube 106 prior to being used in the system 110. The stabilization tube 106 can then be slipped-on or pulled-over the bioink tube 104 on mandrel system 102. Once the stabilization tube 106 is properly positioned such that braid tube 101 is concentric to the bioink layer 104, the stabilization tube 106 can be pulled out in a direction 107 along the axis of the mandrel 102 to leave behind the braid tube 101 on top of the bioink tube 104. The stabilization tube 106 can be made of any material that can easily release or detach from the braid tube 101, bioink tube 104, or both. The stabilization tube 106 can be made from any one of polytetrafluoroethylene and other suitable materials known to one of ordinary skill. The stabilization tube 106 can also be jiggled, shaken, or otherwise moved back and forth in a transverse direction to encourage the braid tube 101 from detaching from the stabilization tube 106. Other suitable techniques are contemplated for encouraging detachment. Once the stabilization tube 106 is removed, the braid tube 101 can now interface with the concentric bioink tube 104 to form the vascular graft 105.

Figure 1E:
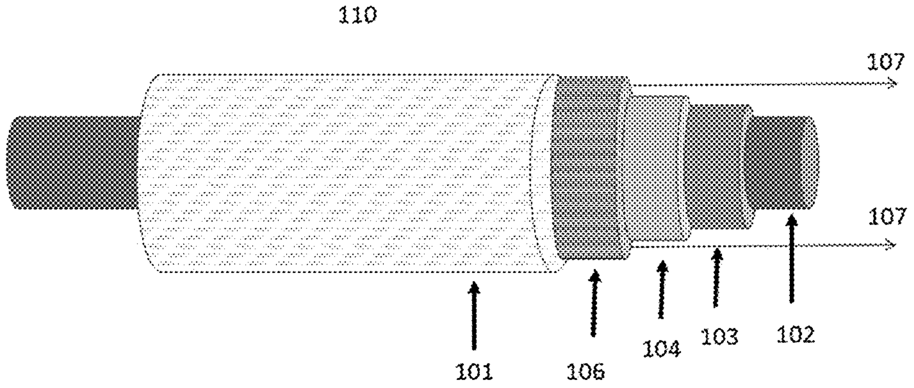

In FIG. 1E, the system 110 can use any one or combination of the stabilization tube 106 and sacrificial layer 103. In one non-limiting embodiment, both the sacrificial layer 103 and stabilization tube 106 are used. The sacrificial layer 103 is first positioned concentrically over the mandrel 102 as described herein, and the bioink tube 104 then positioned over the sacrificial layer 103. The stabilization tube 106 can then be slipped-on or pulled-over the top layer of the bioink tube 104. Alternatively, the braid tube 101 can be pre-positioned on the stabilization tube 106, and the stabilization tube 106 subsequently slipped-on or pulled-over the bioink tube 104. After the combined assembly of the braid tube 101, stabilization tube 106, and bioink layer 103 are concentric to the mandrel 102, the sacrificial layer 103 can be dissolved to provide sufficient radial clearance for the construct 110 to be removed off the mandrel 102. Next, the stabilization tube 106 can be pulled out in direction 107 to leave behind the braid tube 101 on top of the bioink tube 104. Alternatively, the stabilization tube 106 or both the stabilization tube 106 and the sacrificial layer 103 can be dissolved at the same time, or sequentially, using any of the materials and techniques described herein. Once the stabilization tube 106 is removed, the braid tube 101 can now interface with the concentric bioink tube 104 underneath to form the vascular graft 105.

In any embodiment, a second layer of hydrogel such as a second bioink tube (not shown) can be subsequently positioned or deposited on any layer described herein, using any of the additive techniques described herein. For example, a second layer of hydrogel or second bioink tube can be deposited over the braid tube 101 in the system 100. Alternatively, the second layer or second bioink tube can be integrated with the braid tube 101, during any step in forming the construct 110. In certain embodiments, the second layer of hydrogel or second bioink tube can form an outermost layer of the tissue engineered vascular tube.

Figure 2A:
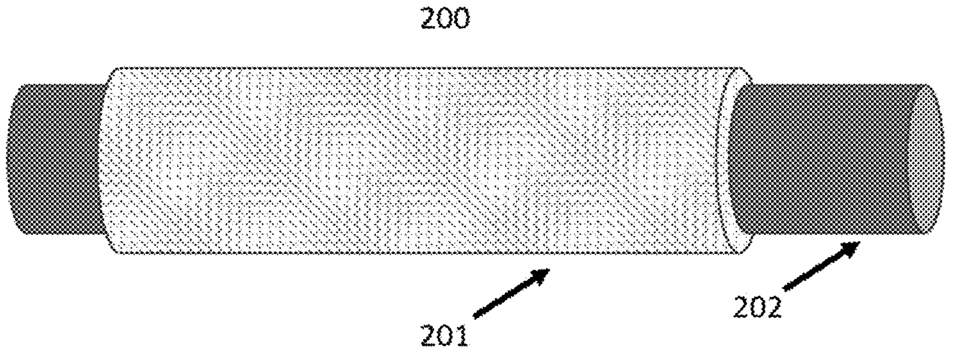
FIGS. 2A-F illustrate a process of generating a tissue engineered vascular graft involving inversion of a braid tube.
Figure 2B:
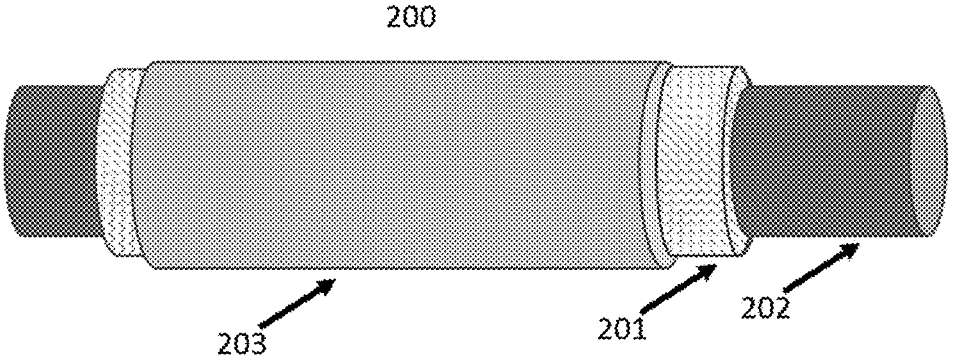
Figure 2C:
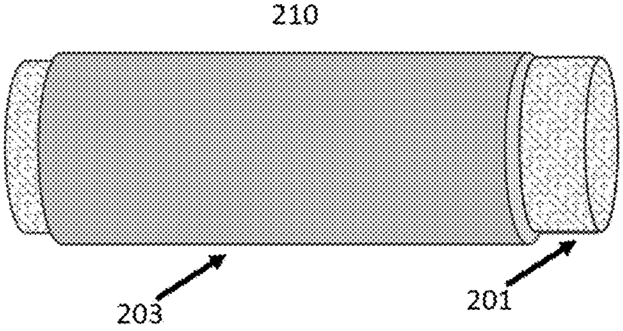
Figure 2D:
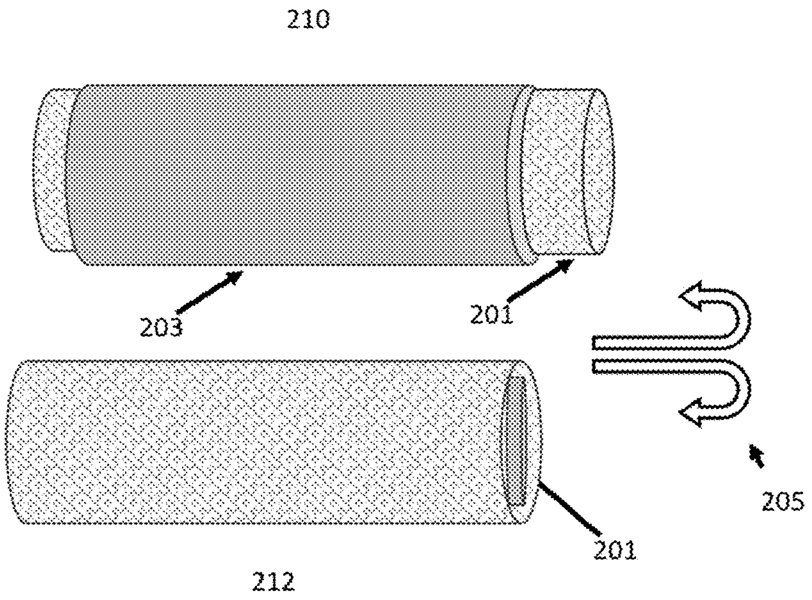

FIGS. 2A-F illustrate an inversion technique used to create a vascular graft 212 as shown in FIG. 2D. In FIG. 2A, a system 200 has a rotating mandrel 202. The system 200 can be an additive 3D printing lathe or similar machine, as described herein, or otherwise known to those of ordinary skill. The braid tube 201 can be single filament or multi-filament and constructed from fabric or any other suitable material, as already described and further provided herein. The braid tube 201 tube can be formed prior to being positioned on the mandrel 202. The braid tube 201 can be made of any non-woven textile, yarn, suture material, woven textile, knitted textile, braided textile of any design or suitable material. The braid tube 201 can be pre-manufactured or formed by a spool over or on another material, and in certain non-limiting embodiments, can be made from any one or combination of a biodegradable, bioabsorbable, or bioinert material, as described herein. The braid tube 201 can be slipped-on or pulled-over one end of the mandrel 200 using any suitable process or machine, as described herein. The braid tube 201 can also be deposited or fabricated directly onto the mandrel 202, as described herein. Optionally, a sacrificial layer (not shown) can be first deposited on mandrel 202 to assist in easily removing a construct 210 off the mandrel 202. The sacrificial layer can be made using any of the materials and techniques described herein.

In FIG. 2B, a bioink tube 203 can be deposited on top of, and concentric to the braid tube 201. The bioink tube 203 can be printed using a bioprinter, 3D printing, or other additive technique onto the braid tube 201, as described herein. The bioink tube 203 can be seeded with additional autologous cells, as described herein. In one embodiment, a controllable moving deposition process such as an automated syringe can evenly distribute and deposit the bioink on the braid tube 201 as the mandrel 202 rotates. The rotating mandrel 202 encourages uniform deposition of bioink material onto the braid tube 201. Once the bioink has been deposited and the bioink tube 203 formed, the construct 210 can be removed from the mandrel 202 as shown in FIG. 2C. As noted, an optional sacrificial layer or release layer, as described herein can be used, to assist in release of the construct 210 off mandrel 202. In a step 205, the construct 210 is inverted such that the bioink tube 203 now forms an inner surface of the inverted construct 210 to form a vascular graft 212 as shown in FIG. 2D. The vascular graft 212 can then be placed into a bioreactor and matured.

Figure 2E:
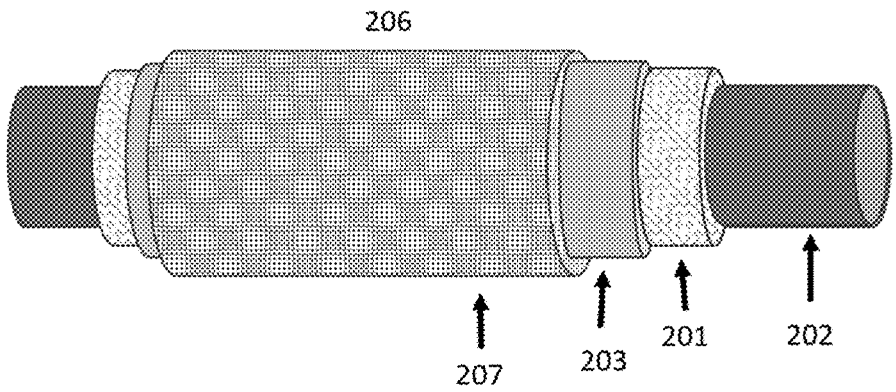
Figure 2F:
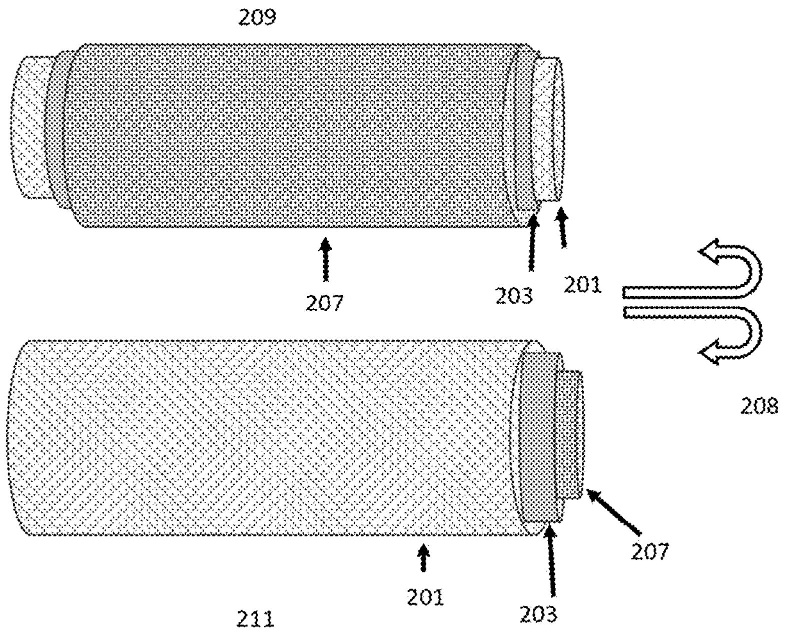

In FIG. 2E, an optional mesh 207 can be positioned over the bioink layer 203 in system 206 prior to removing a construct 209, shown in FIG. 2F, off mandrel 202. The integration of the mesh 207 into hydrogel/bioink can help minimize hyperplasia and also provide structural integrity during the production process. The mesh 207 can be slipped-on, pulled-over, deposited, or fabricated on top of the bioink tube 203 for additional structural integrity. The mesh 207 can provide additional structural support and quickly degrade at a desired time once the manufacturing, or maturation process is complete, as desired. The mesh 207 can also serve as a protective layer. The mesh 207 can be made from a fabric, non-woven fibers, or a porous polymer film. In one non-limiting embodiment, the mesh 207 can be made from a fast-degrading biopolymer to avoid or minimize interaction between the mesh 207 and autologous cells such as endothelial cells that can be seeded onto the bioink tube 203 in the construct 209. The fast-degrading polymer or biopolymer can be any polymeric material that degrades under expected conditions in shorter time relative to another time. The fast-degrading polymer can degrade anywhere from 1 to about 14 days. A person of ordinary skill will understand the relative quickness described as being "fast-degrading" depends on the material, application, and location in which the material degrades. For example, a biopolymer can degrade anywhere from 1 hour to about 72 hours or any other suitable time period acceptable for manufacturing the vascular grafts described herein. In general, the mesh 207 can be made from any suitable material known to those of skill, or as described herein, without limitation.

In FIG. 2F, the resulting construct 209 is a hollow tubular structure with the braid tube 201 on an inner portion of the construct 209 with the bioink tube 203 and mesh 207 layered on top. As described herein, the mesh 207 can be positioned prior to the construct 209 being removed or pulled off the mandrel 202. In step 208, the construct 209 can then be inverted to result in the vascular graft 211. The bioink tube 203 can now form an inner portion, and the braid tube 201 form an outer portion of the vascular graft 211. The vascular graft 211 can then be matured in a bioreactor with inner lumen, i.e., bioink tube 203, seeded with endothelial cells either prior to or during the maturation process to form the vascular graft 211.

Bioink

In any embodiment, the bioink tube can include autologous cells used to create the tissue engineered graft supported by a carrier material such as a hydrogel. The autologous cells can be bone marrow derived mesenchymal stem cells (MSCs), vascular smooth muscle cell (SMCs)-like cells, and endothelial cell (ECs)-like cells. One of skill can derive other possible cells having anti-thrombogenic properties or features that can aid cell implantation and successful host integration.

In any embodiment, the hydrogels can define a desired volume and provide structural integrity for a required time. The hydrogel can be a three-dimensional (3D) network of hydrophilic polymers that can swell in water and hold a large amount of water while maintaining the structure due to chemical or physical cross-linking of individual polymer chains. In any embodiment, the hydrogels can be used as agents for filling vacant spaces, carriers for delivery of bioactive molecules, and 3D structures that act as a support for cells to assist in the formation of tissue. In any embodiment, the hydrogel can be a hydrophilic polymeric network that is cross-linked to produce an elastic structure. Any technique which can be used to create a cross-linked polymer can be used to produce a hydrogel as descried herein. Copolymerization/cross-linking free-radical polymerizations can be used to produce hydrogels by reacting hydrophilic monomers with multifunctional cross-linkers. Water-soluble linear polymers of both natural and synthetic origin can be cross-linked to form hydrogels as known to those of skill in the art. Any of the various polymerization techniques can be used to form gels, including bulk, solution, and suspension polymerization.

Figure 6A:
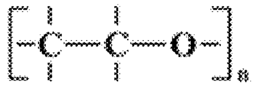
FIGS. 6A-C show embodiments of synthetic hydrogels.
Figure 6B:
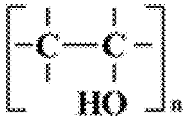
Figure 6C:
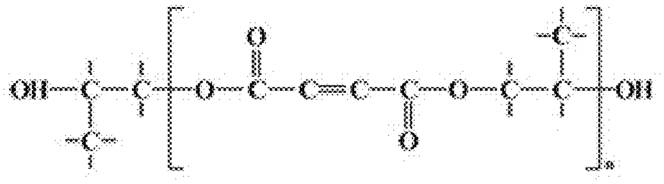

In certain embodiments, the bioink tube can be formed from a natural hydrogel, a synthetic hydrogel, or a hybrid of both synthetic and natural hydrogel. Both synthetic and naturally derived materials can be used to form the hydrogels for tissue engineering scaffolds in the bioink layer. FIG. 6A-C show examples of polymeric synthetic materials which can be used to form hydrogels. Poly(ethylene oxide) (PEO) as shown in FIG. 6A, poly(vinyl alcohol) (PVA) as shown in FIG. 6B and poly(propylene fumarate) (PPF) as shown in FIG. 6C are representative synthetic polymers. In any embodiment, the synthetic hydrogels can be designed to have a specified structure and properties.

Figure 7A:
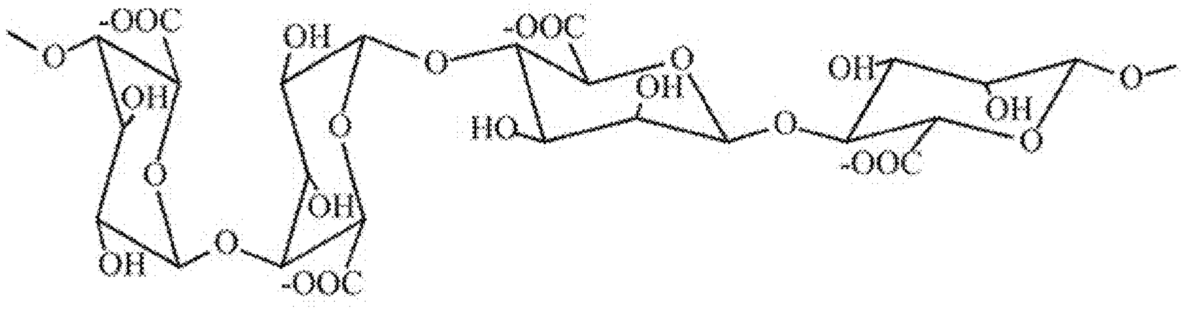
FIGS. 7A and 7B show embodiments of naturally-derived hydrogel-forming polymers.
Figure 7B:
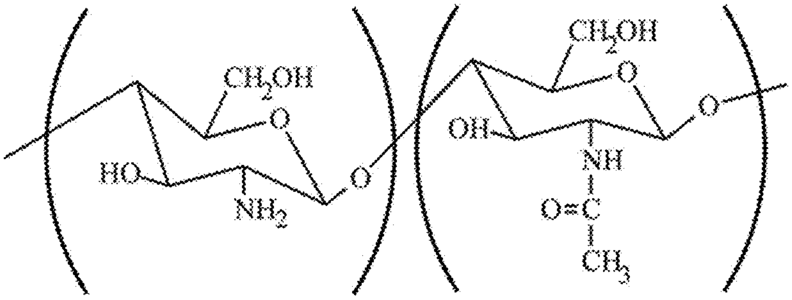

Naturally-derived hydrogel-forming polymers can also be used as tissue engineering scaffolds. For example, extra cellular matrix derived hydrogels can be used. Gelatin methacryloyl (GelMA), fibrin, or a combination of both can be used as the hydrogel. Depending on the printing or additive system used to deposit the bioink tube, hydrogels that are light curable can be used. The bioink tube can also mechanically interlock with the braid tube to ensure integrity. In any embodiment, hydrogel scaffolds based on alginate as shown in FIG. 7A, chitosan as shown in FIG. 7B, and collagen can be used. In any embodiment, a homopolymer such as of poly(2-hydroxyethyl methacrylate) (PHEMA), 2-Hydroxyethyl methacrylate (HEMA), or polyethylene glycol (PEG) can be used. A cross linker such as polyethylene glycol dimethacrylate or TEGDMA (triethylene glycol dimethacrylate). One of ordinary skill can combine different hydrogels suitable for cellular proliferation and function.

3D Printing

Figure 3:
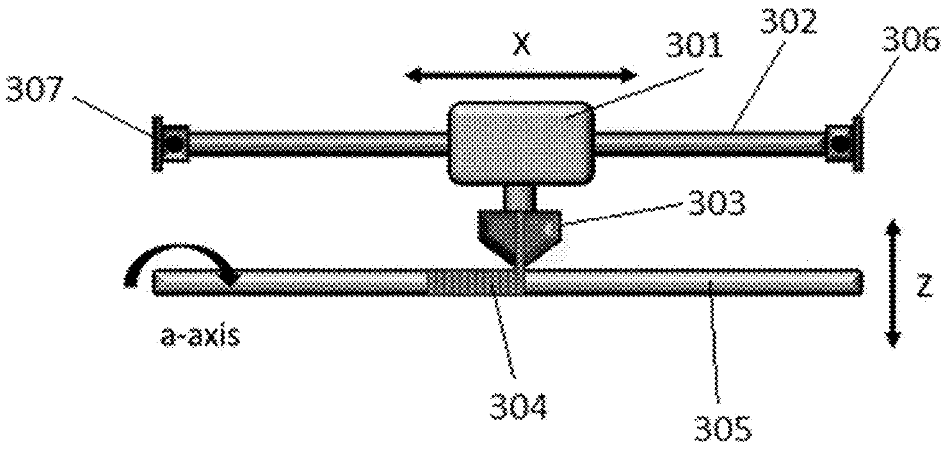
FIG. 3 illustrates a process of depositing bioink on a mesh.

FIG. 3 shows an additive-lathe 3D printer that can layer a material 304 onto a mandrel 305 rotating about axis A. The rotating mandrel 305 can be a component in a bioprinter system. The material 304 can be additively layered on rotating mandrel 305. The mandrel 305 can move up and down in a direction Z to be in closer contact with a block 301 when first depositing material 304 or move away as more layers are added and the diameter of the layered material 304 increases. The mandrel 305 can have a constant outer diameter or a variable outer diameter to create tubes of various geometries such as tapers and the like. The mandrel 305 can be made of stainless steel, and have a desired diameter, such as about 1.5 mm to 12 mm comparable to an inner diameter of a desired vasculature such as a large artery, large vein, or small artery. One of ordinary skill will understand that the mandrel 305 can be made of various tooling and have any desired shape for making tubular structures of any desired diameter matching a desired blood vessel of any type or size.

The material 304 can be deposited on rotating mandrel 305 by a dispenser tip 303 attached to moving block 301. The moving block 301 can move back and forth on shaft 302 in a direction X connected at ends 306 and 307. The filaments of the material 304 can be wrapped around the circumference of the mandrel 305 in a direction perpendicular to the direction X as the mandrel 305 rotates. The filaments of material 304 can be wrapped in any suitable manner, for example, helically with respect to direction X, or in any other appropriate manner, such as helical or diagonal direction. The block 303 can be controlled to deposit droplets or filaments of material 304. The material 304 can include cells suspended in a biodegradable hydrogel, which can adhere to an adjacent filament of material 304, or any of the polymers, and biopolymers described herein. The moving block 301 can move back and forth on shaft 302 multiple times, wrapping one or more layers of material 304. In this manner, layers of material 304 can be additively built on mandrel 305. The block 301 can be directed to contain other types of material in sequential form. For example, the dispenser tip 303 can first extrude material for a sacrificial layer and then subsequently a bioink. Alternatively, any known 3D printing methods for adding material 304 to a mandrel 305 can be used.

Dip Casting and Slot Coating

Figure 4:
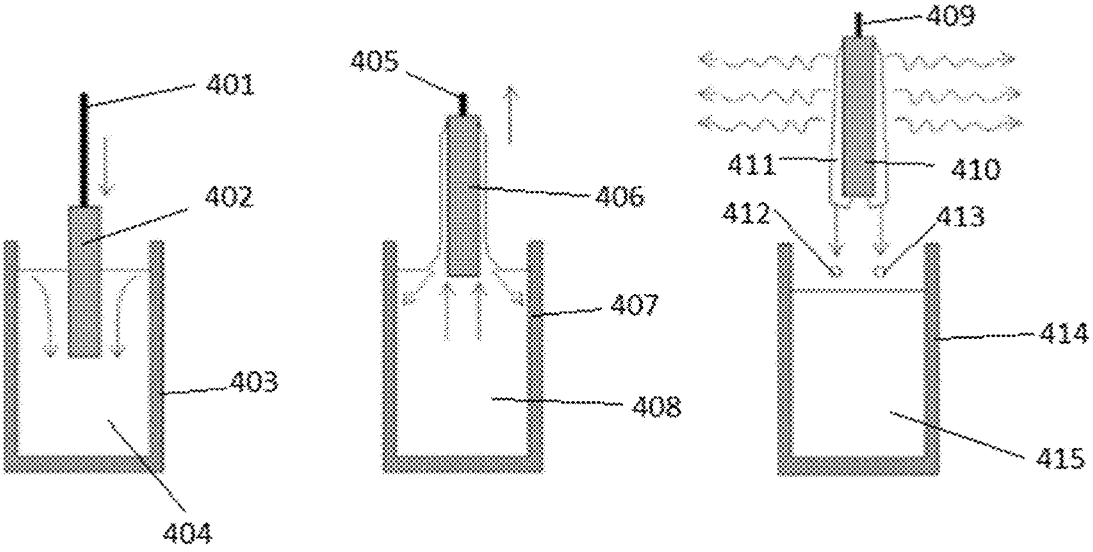
FIG. 4 illustrates a process of dip-coating.

FIG. 4 shows a dip casting process. In any embodiment, any of the materials used for the vascular grafts can be fabricated using the described dip casting process. For example, a rod 401 can be connected to component 402 that forms the cast for a tubular structure. The rod 401 can move vertically up and down to dip component 402 into vat 403 containing a solution 404. The rod 401 can be controlled to move at a constant or variable speed. The component 402 can be immersed into solution 404 and then raised wherein the component 402 is now covered in a material layer 406. For example, the solution 404 can contain a viscous polymer solution or liquid PTFE. The rod 401 can be lowered to immerse the component 402 into solution 404. The component 402 can be dipped as many times as desired into solution 404 to additively build layers to form a tube on rod 401. The drying process of the component 402 can be performed by leaving the component 402 in a vertical position. The dip casting process can be adjusted based on the desired curing time and material properties of the solution 404. The viscosity and temperature of the material, manufacturing environment, and curing time can be adjusted as desired. For example, a sacrificial layer can form on the rod 401 after multiple cycles of dipping in a suitable material solution and drying. The rod 401 can also retain an uncoated section 405 and be pulled upwards out of vat 407 and solution 408 for drying, curing, or maturation. In a position 409, the rod 410 covered by material 411 can evaporate to form a coating. Droplet 412 and droplet 413 can fall back into solution 415 in vat 414 to conserve material. A controller can be used to set an upper and a lower position of the component 402, immersion/withdrawal speed of the rod 401, and a submersion period in solution 404, solution 408, or solution 415. Any suitable material can be contained in the described solutions.

In any embodiment, any of the tube and layered materials used for the vascular grafts can be fabricated using slot coating. The process refers to a deposition process whereby a substrate can be coated, or deposited, with a solution, liquid, slurry, or the like by flowing the solution, liquid, slurry, or the like, through a slot or mold of fixed dimensions that is placed adjacent to, in contact with, or onto the substrate onto which the deposition or coating occurs. Slot coating can be used to coat or deposit a liquid film onto a substrate for mating a flat mesh or patch, or onto a mandrel to make a tubular structure. The film thickness can be controlled by a desired flow rate and speed.

Braid Tube

The manufacturing method and material properties for the braid tube can be selected based on desired flexibility, suture retention, pore structure and size, and radial compliance properties. The braid tube can be made of any non-woven textile, yarn, suture material, woven textile, knitted textile, braided textile, of any design or suitable material. The braid tube can be pre-manufactured or formed by a spool over or on another material. The braid tube can be made of any non-woven textile, yarn, suture material, woven textile, knitted textile, braided textile of any design or suitable material. The braid tube can be pre-manufactured or formed by a spool over or on another material. In certain embodiments, the braid tube can be cell-friendly; in other words, the braid tube does not leach out an unacceptable amount of toxic chemical substances. In certain non-limiting embodiments, the braid tube can be biodegradable, bioabsorbable, or biostable.

In any embodiment, the braid tube can be created from any combination of biostable polymers, such as polypropylene or polyester or combinations thereof. Alternatively, the braid tube can be constructed from bioabsorbable polymers such as poly(glycolic acid) (PGA) and polylactide (PLA) homopolymers, or copolymers of PGA, PLA, polycaprolactone (PCL), poly(trimethylene carbonate) (PTMC), and/or polydioxanone (PDO), or combinations thereof. If a biodegradable polymer is chosen, the braid tube can degrade in a range from 6 to 24 months. Some candidate materials are polyglycolic acid, polylactic acid, polydioxanone, and polycaprolactone. The biodegradable materials can used in pediatric applications, where patient growth can be expected.

Biostable means that the material will not significantly degrade during the useful life of the device. Biostable braid tubes can also be made from metals or metallic alloys, such as platinum and its alloys, tantalum and its alloys, cobalt-chrome alloys, i.e., MP35N®, or nickel-titanium shape memory alloys, i.e., Nitinol. The biocompatibility of metal braids can be improved by adding an anti-thrombogenic coating, i.e., Shield Technology™.

In certain embodiments, a commercially available suture material such as polydioxanone, polycaprone glycolide, vicryl/vicryl, polyglactin 910, lactomer 9-1, Nylon™, polypropylene, silk, braided polyester, such as polyethylene terephthalate, polyglyconate, and combinations thereof can be used for the braid tube. Additional suture materials can include an absorbable synthetic polyester made of a glycolide and lactide, a glycolide/lactide copolymer, a mixture of a caprolactone/glycolide copolymer and calcium stearoyl lactylate, or a synthetic polyester made of glycolide (60%), dioxanone (14%), and trimethylene carbonate (26%). In other embodiments, a biostable or bioinert metal such as a Nitinol (NiTi) wire or nickel-titanium wire can be used in the braid tube. Alternative metals are platinum and its alloys, tantalum and its alloys, and cobalt-chrome alloys, i.e., MP35N®. The braid tube can be made from any combination of suitable biostable and/or biocompatible materials known to one of skill in the art.

In any embodiment, the braid tube can be fabricated by any process known to those of skill in the art for creating a porous tubular structure that has sufficiently large pores to mechanically integrate with the hydrogel and allow for cell growth and the formation of a de novo extra cellular matrix. For polymer materials, the braid tube can be constructed by weaving, knitting, or braiding. By tailoring the density in specified regions of the braid tube or support mesh, one of skill can create a vascular graft that is stiffer in one region or on one side than the other. For example, additional braids or material can be used in specified regions requiring a higher stiffness. A vascular graft having different regions of stiffness can be particularly desirable for an A/V shunt where one side of the braid tube has a stiffness matched to arterial tissue while another side has a stiffness matched to venous tissue.

In any embodiment, the braid tube can have a longitudinally extendahle wireframe or woven “finger trap.” In general, the braid tube has a diameter that increases as the ends are brought toward one another, and a diameter that decreases as the ends are moved away from one another. The braid tube can have a cylindrical, helically wound braid, having a common biaxial braid. In this manner, pulling the entire braid from the ends lengthens and narrows the braid tube. The length of the braid tube is obtained by reducing an angle between warp and well threads at their crossing points, that also reduces a radial distance between opposing sides and hence the overall circumference of the braid tube.

In any embodiment, the braid tube can be tailored to possess specified physical properties. For example, the braid tube can have a desired axial and radial stiffness by modifying the stiffness of the filaments used, and the loop and/or pore size of the braid tube. The braid tube can possess elasticity about the tube’s radius such that braid tube can be pulled over the bioink tube without damaging the bioink while positioned on the mandrel. The braid tube can be stretched after application, placing the braid tube in intimate contact with the bioink tube.

In any embodiment, the void size of the braid tube can be selected for optimal density of autologous cells encapsulated in the hydrogel. The void size can be selected based on desired cell function, nutrients, and oxygen feed into a bioreactor during maturation, as described further herein. In any embodiment, the open voids of the braid tube can provide for an interpenetrating tissue geometry where the growing tissue inside a host can encapsulate a strut of the scaffold material. The tissue interpenetrating into the braid tube can use the strength of the scaffold rather than the interfacial adhesion between the scaffold material and the maturing tissue at the implantation site.

In any embodiment, the braid tube can also assist nutrient transfer into the tissue engineered constructs and speed host tissue integration and vascularization. In any embodiment, the scaffold can degrade at a desired time after tissue maturation and implantation. Hence, the braid tube strength can be used to secure the engineered tissue construct into place but degrade over time as the construct fully integrates into host tissue. In any embodiment, the cell maturation kinetics inside a bioreactor can be distinct from the degradation kinetics of the braid tube inside the host. The bioreactor cultured cells can mature into a tissue that interpenetrates the knitted or braided mesh structure of the braid tube. The knitted mesh structure of the braid tube can be selected for desired erosion kinetics that can occur after a tissue maturation in a bioreactor, implantation, and eventual host integration. The selected properties can assist in the tissue engineered tissue to be sutured securely in the host location but degrading or being absorbed by the host after a suitable time. As noted above, such requirements can be particularly important for pediatric applications.

In any embodiment, three or more filaments using the same or different materials can be intertwined in a diagonally overlapping pattern to form a braid tube. In any embodiment, warp knitting, and weft knitting can be used to create the braid tube. Warp knitting forms loops (wales) in a length of the braid tube, while weft knitting forms loops (courses) in the width or cross of the braid tube. Braids can be formed over mandrels of varying shapes to produce a net-like shaped structure. Any number of a combination of filaments, yarns, or wires from 3 or more ends can be used to create the braid tube. The braid tube can have high radial expansion, strength, flexibility, and controlled porosity determined on various parameters known and adjusted by one of skill in the art.

Figure 5:
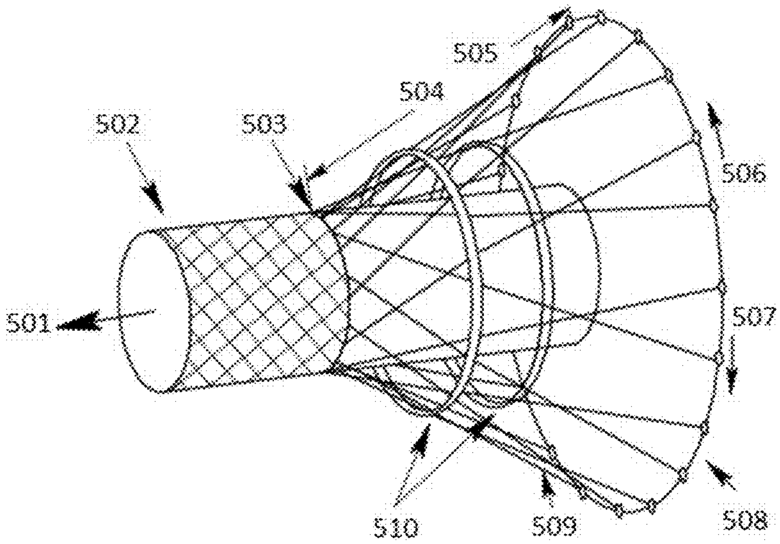
FIG. 5 illustrates a process of braiding.

For example, a braid tube 502 can be constructed by braiding the filaments 509 as shown in FIG. 5. A mandrel 501 can advance through a plane of a rotating carrier spindle platform 508, thereby forming a length of the braid tube 502. As the mandrel 501 rotates, the filaments 509 can intertwine at a braiding front 503. The filaments 509 can be directed by guide rings 510 along a convergence zone along at a line 504 and a line 505. The carrier spindle platform 508 can move in a direction 506 for waft filaments and in a direction 507 for weft filaments. Adjusting the guide rings 510 and speed of rotation, one of ordinary skill can adjust the size of the pore of the braid tube 502.

In any embodiment, the braid tube 502 can be braided in combination with a 3D printing technique. For example, an additive 3D lathe can first deposit a poloaxmer sacrificial layer on mandrel 501; then, the rotating carrier spindle platform 508 can be positioned over mandrel 501 to create the braid tube 502. The filaments 509 can be a monofilament or multi-filament material. The pore size of the braid tube 501 can be between 0.2 and 5.0 mm to allow a bioink tube to interact with the braid tube. The pore size can be selected for proper density of the hydrogel encapsulated cells in the bioink tube, based on necessary cell function, nutrient requirements, and oxygen feed. The braid tube 502 can have a radial compliance between 1% and 20% 1/100 mmHg, selected to roughly match the elasticity and stiffness of the target tissue or organ. One of skill in the art can select an elasticity based on the target tissue or organ.

In any embodiment, weaving can be used to interlace filaments and/or wires over and under each other, oriented at a specified angle to create a stable structure. In any embodiment, knitting can be used to interlock a series of loops of one or more filaments. The braid tube can be manufactured by interlacing warp and weft yarn. Warp knitting can be used to create a desired geometric structure with controlled elasticity in both directions of the braid tube. Weft knitting can be used to control thickness, provide consistent pore size and shape, and desired elongation and recovery properties. In any embodiment, woven mesh fabrics can be used to create the braid tube.

In any embodiment, nonwoven structures produced by interlocking or bonding of fibers can also be used to create the braid tube. The nonwoven mesh structures can have a micro-porous structure. The nonwoven mesh structures can provide for fibrous tissue ingrowth and reduced adhesion. Although described as nonwoven, the braid tube encompasses the described nonwoven structure containing interlocking or bonding fibers.

Strength Measurements

In any embodiment, the tissue engineered vessels can withstand a normal physiological arterial pressure in the range of 80-120 mm Hg (10.6-016 kPa) range or a burst strength of 1680 mm Hg (224 kPa).

Notably, the tissue engineered vessels can each have sufficient biomechanical properties as described in Table 1. Table 1 provides desired mechanical properties of tissue engineered blood vessels (TEBV).

TABLE 1

| Vessel Type | Burst Pressure (mmHg) | Compliance (%)* | Suture Retention (gf) | Wall Thickness (μm) |
|---|---|---|---|---|
| TEBV (4.5 mm ID) | 3,468 ± 500 (n = 5) | 1.5 ± 0.3 (n = 3) | 162 ± 15 (n = 9) | 407 ± 49 (n = 5) |
| TEBV (1.5 mm ID) | 3,688 ± 1865 (n = 9) | ND | ND | 200 ± 41 (n = 3) |
| Human Saphenous Vein | 1,680-2,273 | 0.7-1.5 | 196 ± 2 (n = 7) | ~250 |
| Human Artery | 2,031-4,225 (n = 13) | 4.5-6.2 | 200 ± 119 (n = 9) | 350-710 |

*Calculated for a pressure change from 80 to 120 mmHg

As shown in Table 1, the tissue engineered constructs can have suitable compliance measurements as described herein. Compliance can be measured as defined in ANSI/AAMI/ISO 7198:1998/2001 "Cardiovascular implants—tubular vascular prostheses" (ANSI 7198). The ANSI 7198 standard describes testing methods for vascular grafts. The ANSI 7198 standard requires that segments of vessels approximately 6 cm in length are tensioned to 0.460 N and pressurized with phosphate-buffered saline (PBS). High resolution digital images can be recorded at 50 and 200 mmHg and used to measure the external diameter. Small ringlets from the same vessels can be fixed in formalin prior to testing to obtain geometry at rest from histology cross sections. The inside diameter and wall thickness values at rest can be obtained by analyzing calibrated magnified pictures of the histology slides. Assuming an incompressible wall, compliance can be calculated as follows, and reported as % per 100 mmHg as specified in the ANSI 7198 standard (Eq.1):

$$\frac{\%\ \text{compliance}}{100\ \text{mmHg}} = \frac{(Rip2 - Rip1)/Rip1}{p2 - p1} \times 10^4$$

where p1=lower pressure, p2=higher pressure, and Ripx=internal radius at pressure x, and is calculated from (Eq.2):

$$Ripx = \sqrt{R_{opx}^2 - (R_i + t_0)^2 + R_i^2}$$

where Ropx=measured external radius at pressure x, Ri=measured internal radius at rest, t0=measured wall thickness at rest.

As shown in Table 1, the tissue engineered constructs can have suitable burst pressure strength as described herein. In any embodiment, burst pressure can be specified by ANSI 7198. Segments of vessels approximately 6 cm in length can be cannulated and pressurized with PBS at a rate of 80-100 mmHg/s until failure. A custom LabView (National Instruments, Inc.) data acquisition system in conjunction with a digital pressure gauge (PG10000, by PSI-Tronix) and a computer can be used to record the pressure at a sampling rate of 3 Hz. The maximum uniform pressure exerted at the right angle to the plane of material which results in ruptures under standardized testing conditions is known as bursting strength.

As shown in Table 1, the tissue engineered constructs can have suitable suture retention strength as described herein. In any embodiment, suture retention can be specified by ANSI 7198. Segments of vessels approximately 15 mm in length can be cannulated onto a vertical metal mandrel which is attached to a base weighing 2 kg, and placed on a digital scale. A single 2 mm bite of 5-0 prolene suture with BV-1 needle (Ethicon Inc.) can be placed at an end of the vessel segment, and pulled out at a constant rate of 120 mm/min until failure. The force curve can be measured digitally using a LabView data acquisition system sampling the scale output at 5 Hz. The test can be repeated two more times on the same sample at locations 120 degrees apart to obtain three values for each vessel test segment.

Notably, suture retention strength can also be important when connecting the tissue engineered constructs to a fixture in a bioreactor when axial and hydraulic loading is imposed on the tissue engineered constructs. In any embodiment, the tissue engineered constructs have sufficient suture retention properties to ensure that the constructs are suitably fixated or orientated in a desired direction in the bioreactor when subject to pressure and flow of solutions.

Tissue Engineered Vessels

In any embodiment, a tissue engineered blood vessel having an inner diameter of 4.5 mm can have a compliance (%), calculated for a pressure change from 80 to 120 mmHg (using Eq.1), in a range of 1.2 to 1.8. In any embodiment, a tissue engineered blood vessel having an inner diameter of 1.5 mm can have a compliance (%) in a range of 1.3 to 1.7. In any embodiment, a tissue engineered vein can have a compliance (%) in a range of 0.7 to 1.5. In any embodiment, a tissue engineered blood vessel of any diameter can have a compliance (%) in a range of 4.0 to 7.0.

In any embodiment, a tissue engineered blood vessel having an inner diameter of 4.5 mm can have a burst strength in a range of 2,500 to 5,000 mmHg. In any embodiment, a tissue engineered blood vessel having an inner diameter of 1.5 mm can have a burst strength in a range of 1,500 to 6,000 mmHg. In any embodiment, a tissue engineered vein can have a burst strength in a range of 1,200 to 6,000 mmHg. In any embodiment, a tissue engineered blood vessel of any diameter can have a burst strength in a range of 1,500 to 5,000 mmHg.

In any embodiment, a tissue engineered blood vessel having an inner diameter of 4.5 mm can have a suture retention strength in a range of 125 to 200 gf. In any embodiment, a tissue engineered blood vessel having an inner diameter of 1.5 mm can have a suture retention strength in a range of 125 to 200 gf. In any embodiment, a tissue engineered vein can have a suture retention strength in a range of 175 to 250 gf. In any embodiment, a tissue engineered blood vessel of any diameter can have a suture retention strength in a range of 50 to 350 gf.

A/V Shunt

In an A/V shunts graft, one side can be connected to an artery and the other side to a vein. In any embodiment, a first side of the tissue engineered graft can have ends matched to radial stiffnesses for arterial tissue and venous tissue. For example, a density of the braid tube on one end can be higher, and therefore stiffer than another end.

In any embodiment, an A/V shunt can have a compliance (%) in a range of 4.0 to 7.0 on an arterial end, and a compliance (%) in a range of 0.7 to 1.5 on a venous end calculated from a pressure change from 80 to 120 mmHg (Eq.1). In any embodiment, an A/V shunt can have a have a burst strength in a range of 1,200 to 6,000 mmHg. In any embodiment, an A/V shunt can have a suture retention strength in a range of 125 to 200 gf on an arterial end, and a suture retention strength in a range of 175 to 250 gf on a venous end.

In any embodiment, the described engineered tissues can also be used for organoids for therapy development and testing to reduce animal testing.

In any embodiment, the tissue engineered grafts can have one or more tissue stabilization anchors to secure the construct to surrounding tissue. The stabilization anchors can be a hook, loop, or latch. The stabilization anchors can also be sutures, pins, Velcro-like hooks, and the like. The stabilization anchor can form any part of the construct and be integrated into a supporting structure such as a fabric, braid, mesh, scaffold and the like. In any embodiment, the described supporting structure can have one or more of the described stabilization anchors positioned in the mesh, scaffold, fabric, or braid portions to assist in integration with another material, such as a bioink or native tissue. The stabilization anchors can be positioned throughout the mesh, scaffold, fabric, or braid portions to provide adhesion points for an interpenetrating network between a first material and a second material. For example, the first material can be a bioink and the second material can be a braided polymer or suture material. In another example, the first material can be a braided polymer or suture material, and the second material native tissue.

In particular, the stabilization anchors can aid in the integration of any of the described tissue engineered constructs into host tissue after implantation or surgical placement. In certain embodiments, the material containing the stabilization hooks can degrade over time in vivo. The stabilization anchors can provide a mechanism to stabilize the engineered graft across an implant location as tissue ingrowth occurs. For example, hook knitting can be used to latch onto a surface area of tissue on an organ surface to encourage mechanical integration. In any embodiment, the scaffold can contain cells that are bio-printed or otherwise deposited into a void area of the scaffold.

Bioreactor/Maturing

The tissue engineered vascular grafts can be matured in a bioreactor under pulsatile hydraulic and axial loading until desired properties are obtained. In any embodiment, a pulsatile hydraulic load acting in the inner lumen can be applied for a tubular structure. The tissue engineered vascular grafts can be seeded with cells at either a pre- or post-implantation stage. The cells can be endothelial cells and vascular smooth muscle cells and fibroblasts, as well as their progenitor cells and associated stem cells. Any other cells known to possess anti-thrombogenic properties, minimize platelet aggregation, or clot formation can be used. The constructs can be non-immunogenic. The cells can also be remodeled under certain flow conditions and produce extracellular matrix proteins such as collagen and elastin.

In any embodiment, the tissue engineered vascular grafts can be seeded using passive techniques. A cell suspension of cells can be pipetted directly onto a lumen of a vascular graft in any method known to one of ordinary skill. After application of the cell suspension to the graft, the construct can be incubated with media to allow for cell attachment. In any embodiment, an interior diameter of the bioink tube can be flushed with endothelial cells in the bioreactor. In other embodiments, cells can be seeded and adhered to a support structure with a biological glue. Fibrin or fibronectin can be used as the biological glue. Other adhesive coatings such as collagen, laminin, and plasma can also be used. Alternatively, ligands specific to particular cell types, such as, biomimetic surfactant polymers derived from one of the heparin-binding domains of fibronectin that promote adhesion and growth can be used. In other embodiments, cells can be adhered to a scaffold by using tropoelastin and fibrillins. The various coating methods can be implemented by dipping the scaffold into the glue or by applying pulsatile perfusion onto the scaffold with the biological glue.

In any embodiment, the tissue engineered vascular grafts can be seeded using dynamic techniques. Cell can be seeded by inducing hydrostatic forces, such as rotational or by creating pressure differentials, such as vacuum seeding. The techniques can increase cell seeding efficiency, uniformity, and/or penetration of the scaffold. For example, the described tissue constructs can be rotated about an axis in a cell/medium suspension or spun along with a cell/medium suspension at speeds and times known to those of skill in the art to produce a desired result. The described tissue constructs can also be subject vacuum pressure to force a cell suspension through pores or void spaces of the scaffold.

During maturation, a cyclic force, such as axial tension, can be applied to the constructs. In one non-limiting embodiment, a cell growth medium can be flowed through an inner lumen of a hollow tubular structure containing autologous cells seeded thereon. The cell growth medium can include water, nutrients for the cells and cell signaling chemicals. The flow can replicate physiological conditions to induce remodeling of the cells. For example, a natural diastolic and systolic pressure for hydraulic loading can be provided, such as a pressure amplitude with lower value to 20 mmHg and an upper value of 120 mmHg and applying an axial strain amplitude anywhere from about 0 to 12% strain (Syedain, Zeeshan H., et al. "Implantable arterial grafts from human fibroblasts and fibrin using a multi-graft pulsed flow-stretch bioreactor with noninvasive strength monitoring." Biomaterials 32.3 (2011): 714-722).

One of skill can also determine suitable flow rates, timing, periods. After maturation, the tissue engineered vascular graft can be implanted into a patient. In any embodiment, a vascular graft can be removed from a mandrel after all layers and tubes are formed thereon. The vascular graft can have braid tube and a bioink tube with endothelial cells incorporated on or inside the bioink tube. The vascular graft can be matured in the bioreactor under defined conditions of oxygen partial pressure and cell growth medium. A pulsatile, axial loading force can be applied to the described vascular graft, and one or more nutrition factors and signaling chemicals can be added to the growth medium in the bioreactor, as described.

One of skill in the art will understand that modifications and variations can be made in the described systems and methods depending upon the specific needs for operation. Various aspects disclosed herein may be combined in different combinations than the combinations specifically presented in the description and accompanying drawings. Moreover, features illustrated or described as being part of an aspect of the disclosure may be used in the aspect of the disclosure, either alone or in combination, or follow a preferred arrangement of one or more of the described elements. Depending on the example, certain acts or events of any of the processes or methods described herein may be performed in a different sequence, may be added, merged, or left out altogether (e.g., certain described acts or events may not be necessary to carry out the techniques). In addition, while certain aspects of this disclosure are described as performed by a single module or unit for purposes of clarity, the techniques of this disclosure may be performed by a combination of units or modules.

What is claimed is:

1. A method for forming a tissue engineered vascular graft, comprising the step of:

printing a sacrificial layer on a rotating mandrel;

printing a liquid bioink on the sacrificial layer to form a bioink tube; and positioning a braid tube concentrically over the bioink tube to form the vascular graft.

2. The method of claim 1, wherein the step of positioning the braid tube is comprised of pulling the braid tube over the bioink tube on the mandrel.

3. The method of claim 1, wherein the step of positioning the braid tube is comprised of interlacing filaments concentrically over the bioink tube on the mandrel.

4. The method of claim 1, wherein the braid tube is expandable to a first diameter and contractible to a second diameter under axial loading.

5. The method of claim 1, wherein the braid tube is any one of a woven, knitted, braided, or non-woven textile.

6. The method of claim 1, wherein the braid tube is made of nitinol.

7. The method of claim 1, wherein the bioink is deposited on the rotating mandrel using 3D printing, dip casting, or slot casting.

8. The method of claim 1, wherein the braid tube is positioned concentrically over a stabilization tube, and further comprising a step of pulling out the stabilization tube once the braid tube is positioned on the bioink tube and leaving the braid tube behind over the bioink tube to form the vascular graft.

9. The method of claim 8, wherein the stabilization tube comprises polytetrafluoroethylene, poloxamer, or combinations thereof.

10. The method of claim 1, wherein the printing of the sacrificial layer and the printing of the liquid bioink comprise additive layering.

* * * * *